(12) United States Patent
Mohammed et al.

(10) Patent No.: US 10,954,200 B1
(45) Date of Patent: Mar. 23, 2021

(54) ANTI-ANGIOGENESIS COMPOUND

(71) Applicant: KING SAUD UNIVERSITY, Riyadh (SA)

(72) Inventors: Yasser Hussein Issa Mohammed, Hajjah (YE); Nabil Ahmed Qassim Al-Zeqri, Riyadh (SA); Ali Mohammed Alsalme, Riyadh (SA); Fahed Ahmed Ali Alharthi, Riyadh (SA); Ismail Khalil Warad, Nablus (PS); Anas Khaled Alali, Nablus (PS); Abdelkader M. Zarrouk, Oujda (MA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 16/663,051

(22) Filed: Oct. 24, 2019

(51) Int. Cl.
*C07D 265/30* (2006.01)
*A61K 31/5375* (2006.01)
*A61P 35/00* (2006.01)

(52) U.S. Cl.
CPC ........ *C07D 265/30* (2013.01); *A61K 31/5375* (2013.01); *A61P 35/00* (2018.01)

(58) Field of Classification Search
CPC .......................... C07D 265/30; A61K 31/5375
See application file for complete search history.

(56) References Cited

U.S. PATENT DOCUMENTS

| | | | |
|---|---|---|---|
| 7,470,709 B2 | 12/2008 | Barsanti et al. | |
| 7,825,132 B2 | 11/2010 | Cai et al. | |
| 8,063,225 B2 | 11/2011 | Gregor et al. | |
| 8,686,005 B2 | 4/2014 | Gregor et al. | |
| 8,946,216 B2 | 2/2015 | Deng et al. | |
| 9,290,503 B2 | 3/2016 | Gregor | |
| 2005/0256157 A1 | 11/2005 | Gesner et al. | |

OTHER PUBLICATIONS

Al-Ghorbani et al., Bioorganic Chemistry, 71, 2017, pp. 55-66 (Year: 2017).*
Al-Ghorbani et al., "Synthesis and biological efficacy of novel piperazine analogues bearing quinoline and pyridine moieties," Russian Journal of Bioorganic Chemistry, 2015, 41(5), 554-561.
Al-Ghorbani et al., "Synthesis and antiproliferative activity of benzophenone tagged pyridine analogues towards activation of caspase activated DNase mediated nuclear fragmentation in Dalton's lymphoma," Bioorganic chemistry, 2016, 65, 73-81.
Saleh et al., "Synthesis, Characterization and Molecular Docking of Novel Quinoline and Pyridine Derivatives," Oriental Journal of Chemistry, 2017, 33(6), 2713-2719.

* cited by examiner

*Primary Examiner* — Laura L Stockton
(74) *Attorney, Agent, or Firm* — Nath, Goldberg & Meyer; Richard C. Litman

(57) ABSTRACT

An anti-angiogenic compound includes 4-Benzyl-N'-(2-(o-tolyloxy) acetyl) morpholine-2-carbohydrazide (BAMC), having the following structural formula:

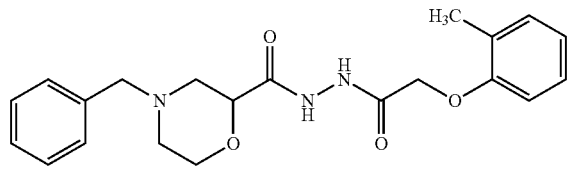

or a pharmaceutically acceptable salt thereof.

10 Claims, 8 Drawing Sheets

ANTI-ANGIOGENESIS COMPOUND

BACKGROUND

1. Field

The disclosure of the present patent application relates to anti-cancer compounds, and particularly to an anti-angiogenesis compound.

2. Description of the Related Art

One of the hallmarks in the advancement of cancer cells is an ability to overcome and acquire resistance to adverse conditions and thereby, become immortal. The search for anti-cancer drugs with minimal side effects has led to the discovery of synthetic molecules with anti-carcinogenic activity. One reason cancer cells escape apoptosis is down regulation of tumour suppressor genes and appearance of oncogenes. Impairment of this native defense mechanism of cancer cells promotes anomalous cellular proliferation and the accumulation of genetic defects, eventually resulting in tumorigenesis and resistance towards cancer drugs.

Killing cancer cells through activation of apoptosis has stimulated interest among researchers. Pharmacological inhibition of vascular endothelial growth factor A (VEGF-A) has been confirmed as an efficient strategy for inhibiting angiogenesis allied with cancers and diverse diseases. Hence, the arsenal for inhibition strategies of VEGF-A is the new emergent field of tumour pathology. Several groups have developed methods for sequestering VEGF, which leads to a signal obstruct via VEGF receptors and subsequently to an inhibition of angiogenesis. Recent studies showed that, in treatment of cancer, DNA is the targeted molecule for chemotherapeutic approach.

Thus, anti-angiogenesis compounds solving the aforementioned problems is desired.

SUMMARY

An anti-angiogenesis compound includes 4-Benzyl-N'-(2-(o-tolyloxy) acetyl) morpholine-2-carbohydrazide (BAMC), having the following structural formula:

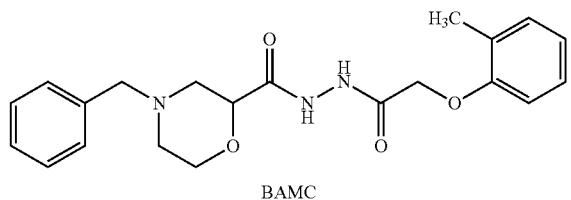 [SMILES: Cc1ccccc1OCC(=O)NNC(=O)C1CN(Cc2ccccc2)CCO1]

BAMC or a pharmaceutically acceptable salt thereof.

The anti-angiogenesis compound can down-regulate the formation of neo vasculature, inhibit production of Vascular Endothelial Growth Factor (VEGF), and induce apoptotic cell death in cancer cells. The anti-angiogenesis compound can be used as an active ingredient of pharmaceuticals for the treatment of cancer.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
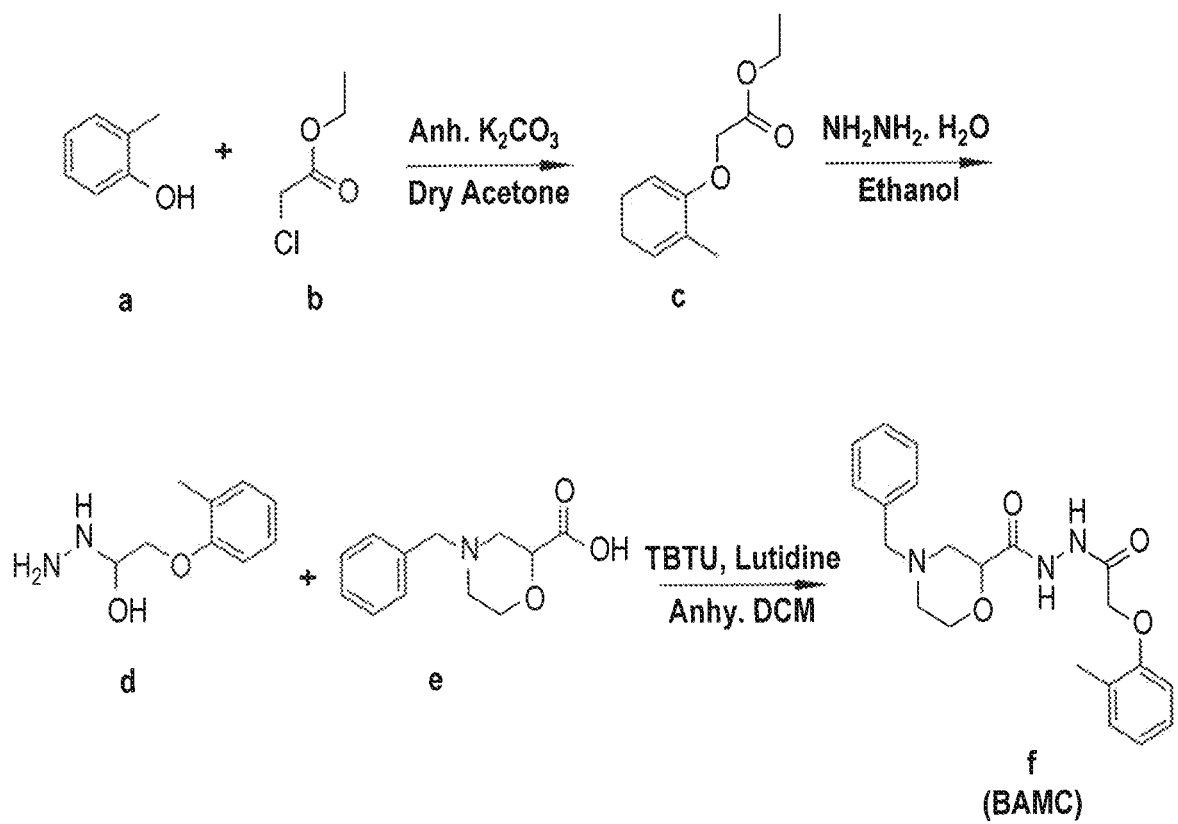
FIG. 1 is an exemplary reaction scheme for synthesizing the anti-angiogenesis compound.

An anti-angiogenesis compound includes 4-Benzyl-N'-(2-(o-tolyloxy) acetyl) morpholine-2-carbohydrazide (BAMC), having the following structural formula:

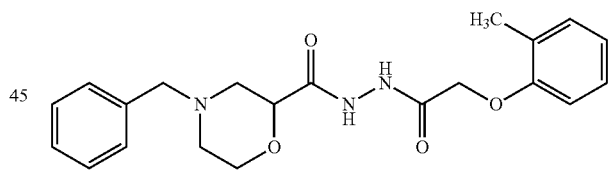

or a pharmaceutically acceptable salt thereof.

The anti-angiogenesis compound can down-regulate the formation of neo vasculature, inhibit production of Vascular Endothelial Growth Factor (VEGF), and induce apoptotic cell death in cancer cells. The compound can be used as an active ingredient of pharmaceuticals for the treatment of cancer.

As described herein, the anti-angiogenesis compound (BAMC) was synthesized by integrating a phenyl morpholine pharmacophore to a phenoxy-acetic hydrazide moiety. The anti-angiogenesis compound was found to elicit apoptotic cell death by degrading genomic DNA of cancer cells and thereby, decreasing ascetic tumor development in mice. Compound BAMC was found to exhibit a promising anti-angiogenesis effect with $IC_{50}$ values of ~5.5 µM. Compound BAMC exhibited very small toxicity (~97 µM) to NIH-3T3 cells. Molecular gene studies suggested involvement of VEGFr receptor, which has been interlinked in signaling and conformed by docking studies. Altogether, these results suggest that compound BAMC is potent and prone to exhibit a cytotoxic effect against cancer cells of different origin.

A pharmaceutically acceptable salt includes any non-toxic salt of the present anti-angiogenesis compound, which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

The anti-angiogenesis compound can be administered to a patient in need thereof. For example, the anti-angiogenesis compound can be used to treat a patient suffering from cancer.

The anti-angiogenesis compound can be administered by any conventional route of administration, including, but not limited to, intravenous, oral, subcutaneous, intramuscular, intradermal and parenteral. Depending on the route of administration, the compounds can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

Also provided is a pharmaceutical composition including an anti-angiogenesis compound. To prepare the pharmaceutical composition, one or more anti-angiogenesis compounds or salt thereof, as the active ingredient, is intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

A therapeutically effective amount of the anti-angiogenesis compound or an amount effective to treat cancer may be determined initially from in vivo assays described herein and adjusted for specific desired anti-angiogenesis compound using routine methods.

The following examples illustrate the present teachings.

Example 1

Cancer Cells

Breast cancer cells (MCF-7), lung cancer cells (A549), Hela cells, and peripheral blood mononuclear cells (PBMC) were purchased from the National Center for Cell Sciences (NCCS), Pune, India. The cancer cells were maintained in Dulbecco's modified eagles medium (DMEM), supplemented with 2 mM 1-glutamine and balanced salt solution (BSS), adjusted to contain 1.5 g/L $Na_2CO_3$, 0.1 mM non-essential amino acids, 1 mM sodium pyruvate, 2 mM 1-glutamine, 1.5 g/L glucose, 10 mM (4-(2-hydroxyethyl)-1-piperazineethane sulfonic acid) (HEPES), and 10% fetal bovine serum (GIBCO, USA). Penicillin and streptomycin (100 IU/100 µg) were adjusted to 1 mL/L. The cells were maintained at 37° C. with 5% $CO_2$ in a humidified $CO_2$ incubator.

Example 2

Test Concentrations

Stock solutions of each compound and positive control were prepared fresh prior to the start of every experiment. A stock solution of each compound was prepared at a concentration of 8 mg/mL in 100% Dimethyl Sulfoxide (DMSO, Sigma Chemical Co., St. Louis, Mo.). Working solutions of each test chemical were prepared by serial dilutions with the appropriate culture media. All the compounds were tested using the required concentrations ranging from 10 to 200 µg/ml.

Example 3

Cell Viability

The inhibitory concentration ($IC_{50}$) value was evaluated using an MTT [3-(4,5-dimethylthiazol-2-yl)-2,5-diphenyltetrazolium bromide] assay. Cancer cells were grown ($1 \times 10^4$ cells/well) in a 96-well plate for 48 h to 75% confluence. The medium was replaced with fresh medium containing serially diluted synthesized compounds, and the cells were further incubated for 48 h. The culture medium was removed, and 100 µL of the MTT [3-(4,5-dimethylthiozol-2-yl)-3,5-diphenyl tetrazolium bromide] (Hi-Media, Mumbai, India) solution was added to each well and incubated at 37° C. for 4 h. After removal of the supernatant, 50 µL of DMSO was added to each of the wells and incubated for 10 min to solubilize the formazan crystals. The optical density was measured at 620 nm in an ELISA multiwell plate reader (Thermo Multiskan EX, USA). The OD value was used to calculate the percentage of viability using the following formula.

$$\% \text{ of viability} = \frac{OD \text{ value of experimental sample} \times 100}{OD \text{ value of experimental control}}$$

Example 4

Trypan Blue Dye Exclusion Assay

The cytotoxic effects of synthesized compounds on various types of cancer cells were determined by trypan blue dye exclusion assay. The cultured cells were treated with the synthesized compounds and incubated for 48 h. After the incubation period, the cells were detached by 0.5% trypan-EDTA solution, harvested by centrifugation at 3000 rpm for 5 minutes and diluted in 1 ml of PBS. Then, 10 µl of trypan blue dye solution was added to each sample and cells were re-suspended. About 20 µl of cell suspensions were carefully and continuously filled in the haemocytometer chamber and viable cells were counted in 1×1 mm squares, four chambers and the average number of cells per square determined. Total viable cells were determined using the following formula, $$\text{Total viable cells} = \frac{A+B+C+D}{4} \times \text{dilution factor}$$

The values were plotted in MS excel version 8.1, graphed and the inhibitory concentration-50 ($IC_{50}$) values were estimated.

Long-term effects of the active compound were determined by colony formation with minor modifications. Briefly, selected cell line MCF-7 (400 cells/well) were exposed to the compound and incubated at 37° C. for 24 h. Surviving colonies were fixed and stained by using 0.5% crystal violet. Visible colonies were observed and colonies were counted and photographed.

Example 5

DNA Fragmentation Assay

DNA damaging studies were carried out according to previously described methods. The DNA damaging activity of the compound on genomic DNA of both control and treated cells were evaluated by Phenol:Chloroform method. Briefly, the cells were first lysed using lysis buffer (50 mM Tris-Hcl, 0.5% SDS, pH 8.0) and incubated for 30 minutes at 370° C. The cell lysate was precipitated by using potassium acetate (8M) and incubated at 4° C. for 1 hr. The supernatant was mixed with phenol:Chloroform:isoamylalcohol at 25:24:1 ratio. This step was repeated thrice. DNA was precipitated by adding ice cold alcohol and precipitated DNA was air dried and dissolved by using appropriate amounts of TE Buffer (pH 8.0). Precipitated DNA was subjected to RNase digestion (2 µg/mL) for 1 hr at 37° C. The obtained DNA was quantified by using nanodrop (Eppendrof Ag 22331 Hamburg 6135EM402331) and equal amounts of (50 µg) of DNA were loaded to 1% agarose gel, observed under uv-trans illuminator, and documented.

Example 6

Cancer Cell Migration Assay

The A549 cells were cultured in a six well plate until they reached a confluence of 60-70%. A scratch was made to form a wound using a micropipette tip and the monolayer was washed with growth medium. Then, 2 ml medium containing different concentrations of test drugs was added to the respective wells, incubated for 48 h, fixed with chilled 70% ethanol and stained with crystal violet (0.4 g/l). Images were taken from random fields at regular time intervals using an inverted microscope (Bresser, Biolux). Finally, the percentage of cell migration was calculated by comparing the final gap width to initial gap width.

Example 7

Caspase-3 Assay

Using CPP32/Caspase-3 Colorimetric Assay Kit, the activated caspase was estimated as per manufacturer's protocol. The buffers used in the experiment were those supplied along with the kit. A549 cells ($8 \times 10^5$ per 12.5 $cm^2$ culture flasks) were seeded with their respective growth medium and incubated for 24 h at 37° C. with/without 5% $CO_2$. Then, confluent cells were added with the respective drug medium while maintaining an untreated group as a control. Cultures were incubated for 6 h, maintaining the same conditions, 0.1 mM Hydrogen Peroxide ($H_2O_2$) and 10 µM standard drug were used as positive control for activation of caspase-3. After treatment incubation, the detached cells in the supernatant were collected, and the adherent cells were trypsinized to add into the respective tubes. Subsequently, tubes were centrifuged at 1500 rpm for 10 min to acquire a cell pellet. A volume of 50 µl cell lysis buffer was added to the obtained cell pellet and incubated on ice for 15 min. followed by centrifugation at 4000 rpm for 5 min. The compound BAMC was transferred to fresh tubes and the protein concentrations of samples were determined by employing Bradford assay. Finally, each protein sample (100 g) from the whole cell protein extracts, diluted to 50 µl with cell lysis buffer, was added in a 96 well plate for the reaction. A volume of 100 µl reaction buffer containing 10 mM dithiothreitol (DTT) was then added to all wells, which was followed by the addition of 5 µl of 4 mM Asp-Glu-Val-Asp (DEVD)-pNA substrate. The plate was then incubated at 37° C. for 90 min. Post-incubation, the plate was read at 405 nm in a Dynex Opsys MRTM Microplate Reader (Dynex Technologies, VA, USA). Percentage caspase-3 activation was calculated using the following formula:

% Caspase-3 activation=[(At−Ac)/Ac]×100

"At" represents the mean absorbance of test wells and "Ac" represents the mean absorbance of the control wells.

Example 8

Determination of the Lethal Dose (LD50)

For the assessment of $LD_{50}$ of the potent synthesized compounds, the 'staircase' method was used. Healthy Swiss albino male mice weighing 27-30 g were employed and were separated into six groups (n=5, each). Potent synthesized compounds were dissolved in DMSO and administered to animals at increasing concentrations of 100, 200, 500, 1000 mg/kg b.w by i.p injections. The mice were then examined constantly for 4 h for general behavioral, neurological, autonomic profiles, and then for 30 minutes for the next 4 h and lastly for death after 24 h. The maximum non-lethal and minimum lethal doses were thus determined. $LD_{50}$ dose of the potent synthesized compounds, such as 25, 50 and 75 mg/kg was selected as the therapeutic dose for the assessment of in vivo anti-angiogenic and anti-cancer activity.

Example 9

Animals and Ethics

The animal models used for the study include healthy Swiss albino male mice weighing 25±2.0 g and Swiss albino male Wistar rat weighing 150±5.0 g. All the animals were grouped separately, housed in polyacrylic cages, and maintained under standard conditions (25±2° C.) with 12±1 h dark/light cycle with water ad libitum and standard food pellets procured from Krish Scientist's Shopee, Bengaluru, India. All procedures for animal experiments were carried out in accordance with the CPCSEA guidelines and approved by the Institutional Animal Ethics Committee, Mahajana Education Center (IAEC/FC/06/2017).

Example 10

Tumor Model

The EAC tumor was obtained from Mahajana Education Center, BOC, in Biotechnology. Microbiology& Biochemistry Mahajana College, Mysore University, Mysore, Karnataka, India, and the same was induced into adult Swiss albino mice i.p and left for the growth.

Example 11

Propagation of EAC Tumor

The EAC tumor bearing mice (donor) were taken on the $12^{th}$ day after tumor transplantation and the ascites fluid was drawn using an 18 gauge needle into a sterile syringe. Then the tumor cell viability was tested by trypan blue exclusion assay and the cells were counted using a haemocytometer. The ascites fluid was suitably diluted to get a concentration of $5 \times 10^6 / 0.2$ ml of tumor cell suspension. This was injected into the i.p cavity of Swiss mice to obtain ascites tumor and the process was repeated every 12 days.

Example 12

Development of Ascites Tumor

Ascites tumor was obtained by injecting $5 \times 10^6$ viable tumor cells into i.p cavity of Swiss mice. Tumor growth was followed by recording the animal weights. These cells grew in the peritoneum of mice, forming an ascites tumor with enormous abdominal swelling and showing a profound increase in body weight. The EAC cells began their exponential growth phase from the $7^{th}$ day after tumor cell injection and the animals succumbed to the ascites tumor burden between 16 to 20 days after injection of tumor cells.

Example 13

Peritoneal Angiogenesis Assay

The effect of potent synthesized compound BAMC on the modulation of neovessel and tumor growth was verified in EAC bearing animals. The EAC tumor bearing mice were grouped separately at two different concentrations (25 and 50 mg/Kg, b.w/i.p) of potent synthesized compounds and individually the groups were treated using a 26 gauge needle. Then, after the onset of tumor on the 4th day, three doses were given on every alternative day. The growth of the tumor was monitored by taking the body weight of the animals every day. Then, control animals were injected with 0.2 ml of saline (i.p) on every alternative day. In each treatment, at least six mice were taken and each experiment was repeated thrice. After the completion of treatment, the animals from each group were sacrificed on the 10th day and the EAC cells along with ascites fluid were harvested and the quantity was recorded. The peritoneum of the mice was cut open and the inner lining of the peritoneal cavity was examined for angiogenesis (vasculature) in compound-treated, tumor bearing mice. Finally, the inner lining of normal mice was also examined for vasculature and photographed using Sony steady shot DSC-W610 camera. These sets of animals were used to study the survivability analysis after treatment until their death.

Example 14

In Silico Molecular Docking Studies

In view of the results of the above-mentioned in vitro experiments, molecular docking studies were performed for substantiating the in vivo results by in silico validation. The synthesized novel molecule BAMC was subjected to molecular docking studies with chembiodraw Ultra 14.0 software which used for building the ligands, including all hydrogen atoms. The compound used for docking was converted into 3D with ChemBio3D Ultra 14.0. For the purpose of in silico, autodock tools programme was used. A conformational search of the ligand, which is considered in one of the applications of multi-conformer docking, was first approved, and all related low energy conformations were then inflexibly located in the binding site. In order to consider the rigid conformer, rotational and translational degrees of freedom were allowed. A series of shape-based filters were used by the autodock process and Gaussian shape fitting was the building block, in which scoring conformation (Sn, $n=S_1 \ldots S_{10}$) depended on binding energies. By using autodock tools-1.5.6 m, in silico study of the inhibitors with VEGFR kinase domain from VEGF [PDB: 3qtk], were performed. In three dimensional atomic coordinates, the proteins and ligands were downloaded and prepared for molecular docking. A method of Lamarckian genetic algorithm (LGA) was applied in the programme which was used to identify appropriate binding modes and conformation of the ligand molecules. One of the major processes of the in silico study was the addition of the polar hydrogen atoms and the assigning of Kollman charges to the protein using autodock tools. Type grid maps were assigned to every single atom in the protein and the ligands. Through this study, a calculation was done for the desolation maps and additional electrostatics. Using LGA, molecular docking simulations were performed as the search algorithm. With the help of PyMol programme, all molecular modeling experiments were carried out with carton and ribbon models.

Ramachandran angles describe the rotations of the polypeptide backbone around the bonds between N-Cα (called Phi) and Cα-C (called Psi). The Ramachandran plot provides an easy way to view the distribution of torsion angles of a protein structure.

Example 15

Synthesis of 4-Benzyl-N'-(2-(o-tolyloxy) acetyl) morpholine-2-carbohydrazide (BAMC)

An exemplary reaction scheme for synthesizing BAMC is provided in FIG. 1. The parent compounds phenoxy acetic ethyl esters c were obtained by refluxing substituted phenol a with b and confirmed by the disappearance of OH stretching and appearance of carbonyl stretching band for the ester group in the IR absorption spectra. The proton NMR observations revealed that broad singlet for OH proton disappeared and a triplet and quartet for $CH_3$ and $CH_2$ protons, respectively, appeared. The compound c, on treatment with hydrazine hydrate, afforded phenoxy-acetic hydrazide d, which was established by the appearance of $NH_2$ stretching band of amide in the IR spectra. In proton NMR, the appearance of $NH_2$ and NH protons and disappearance of triplet and quartet peaks for $CH_3$ and $CH_2$ protons, respectively, confirmed the formation of the product. The corresponding final compounds BAMC were successfully synthesized by coupling compound d with 4-benzylmorpholine-2-carboxylic acid 5 using TBTU (O-(benzotriazol-1-yl)-N,N,N,N-tetramethyluroniumtetrafluoroborate) as a coupling reagent and lutidine as a base. The structures of the newly synthesized compounds were assigned on the basis of their spectroscopic data; IR, NMR, LC-MS and C, H, N analysis. In the IR spectra, compound 6c was confirmed by the appearance of one more peak for carbonyl group and disappearance of the $NH_2$ absorption peak. In addition, $^1H$ NMR spectra showed disappearance of $NH_2$ protons, appearance of one more NH proton, an increase in four aromatic protons with earlier aromatic proton peaks, and appearance of three characteristic bands corresponding to seven protons of morpholine ring which clearly evidence the formation of compound BAMC. The mass spectra of compound BAMC gave significant stable m/z 384 (M+). Further, the target compound BAMC was clearly confirmed by $^{13}C$ NMR.

Example 16

Synthetic Procedure for Phenoxy Acetic Ethyl Ester Derivatives

A mixture of methyl phenol (a, 0.05 mol) and (b, 0.075 mol) in dry acetone (40 ml) with anhydrous potassium carbonate (0.075 mol) were refluxed for 8-10 h. The reaction mixture was cooled and solvent removed by distillation. The residual mass was triturated with cold water to remove potassium carbonate, and extracted with ether (3×30 ml). The ether layer was washed with 10% sodium hydroxide solution (3×30 ml) followed by water (3×30 ml) and then dried over anhydrous sodium sulfate and evaporated to afford compound c.

O-tolyloxy-acetic acid ethyl ester (c)

Yield 83%; FT-IR $(cm^{-1})$: 1735 (C=O), 1279 (C—O—C); $^1H$ NMR (CDCl3): σ1.35 (t, 3H, $CH_3$ of ester), 2.16 (s, 3H, $CH_3$), 4.31 (q, 2H, $CH_2$ of ester), 5.01 (s, 2H, $CH_2$), 6.82 (d, J=8.80 Hz, 1H, Ar—H), 7.37 (d, J=7.40 Hz, 1H, Ar—H), 7.54 (t, J=8.80 Hz, 2H, Ar—H), LC-MS m/z 195 (M+). Anal. Calcd. for $C_{11}H_{14}O_3$: C, 68.02; H, 7.27. Found: C, 68.14; H, 7.16%.

Example 17

Synthetic Procedure for Phenoxy-Acetic Acid Hydrazide Derivatives (d)

Hydrazine hydrate (0.045 mol) was added to the solution of compound c (0.03 mol) in ethanol (20 ml) and the reaction mixture was stirred at room temperature for 7 h. Reaction completion was monitored by thin layer chromatography using hexane:ethylacetate (2:1) as the mobile phase, and allowed to stand overnight. The white crystals d formed were filtered, washed and after drying recrystallized from ethanol.

O-tolyloxy-acetic acid hydrazide (d)

Yield 81%; mp 116-118° C.; FT-IR (KBr, $cm^{-1}$): 3310 ($NH_2$), 3217 (NH), 1672 (C=O); $^1H$-NMR (CDCl$_3$): δ 2.16 (s, 3H, $CH_3$), 3.83 (d, 2H, $NH_2$), 5.03 (s, 2H, $OCH_2$), 6.82 (d, J=8.80 Hz, 1H, Ar—H), 7.37 (d, J=7.40 Hz, 1H, Ar—H), 7.54 (t, J=8.80 Hz, 2H, Ar—H), 8.41 (t, 1H, NH); LC-MS m/z 181 (M+1). Anal. Calcd. for $C_9H_{12}N_2O_2$: C, 59.99; H, 6.71; N, 15.55. Found: C, 60.07; H, 6.65; N, 15.62%.

Example 18

Synthesis of phenyl 2-(4-benzylmorpholine-2-carbonyl)hydrazine-1-carboxylate (f)

Phenoxy-acetic acid hydrazide derivatives (d, 2 mmol) in dry DCM (30 ml) was stirred at 25-30° C., and then lutidine (3 mmol) was added, followed by the addition of 4-benzylmorpholine-2-carboxylic acid (e, 2 mmol). The reaction mixture was stirred at the same temperature for 30 min., then cooled to 0-5° C. and TBTU (2 mmol) was added over a period of 30 min., maintaining the temperature below 5° C. The reaction mass was stirred overnight and monitored by TLC using ethyl acetate; Hexane (4:1) as the mobile phase. The solvent was evaporated at reduced pressure, quenched by the addition of crushed ice and the obtained solid was filtered, dried and recrystallized from ethanol to afford compounds 6 in good yield.

4-Benzyl-N'-(2-(o-tolyloxy)acetyl)morpholine-2-carbohydrazide (6)

Yield 72%; M.P160-162° C.; FT-IR (KBr, $cm^{-1}$): 1650 (C=O), 1678 (amide, C=O), 3275-3360 (NH—NH); $^1H$ NMR (DMSO-d6): δ 2.16 (s, 3H, CH3), 2.68 (t, 4H, J=8.0 Hz, NCH2 of morpholinering), 3.57 (s, 2H, NCH2), 3.57 (t, J=7.80 Hz, 1H, CH of morpholine ring), 4.09 (t, J=7.80 Hz, 2H, OCH2 of morpholine ring), 5.20 (s, 21H, OCH2), 6.85-7.29 (m, 9H, Ar—H), 9.75 (bs, 1H, NH), 9.91 (bs, 1H, NH); 13C NMR (DMSO-d6): δ 15.41, 55.76, 59.70, 64.70, 90.10, 117.41 127.11, 128.80, 130.91, 138.60, 156.22, 166.30, 169.90; LC-MS m/z 383 (M), 384 (M+). Anal. Calcd. for $C_{21}H_{25}N_3O_4$: C, 65.78; H, 6.57; N, 10.96, Found: C, 65.80; H, 6.59; N, 10.98%.

Example 20

Cytotoxicity

BAMC was screened against multiple cancer cell types of different origin. Initially, the anti-proliferative efficacy of phenyl morpholine analogue BAMC bearing morpholine and phenoxy nucleus was evaluated against human cancer cells, such as MCF-7, Hela, A549, EAC and PBMC cells by performing MTT and trypan blue assays. Results of this study are provided in Table 1 below.

TABLE 1

Anti-proliferative Activity of BAMC against Cancer Cells

| | IC$_{50}$ value (µM) against MCF-7 cells | | IC$_{50}$ value (µM) against Hela cells | | IC$_{50}$ value (µM) against A549 cells | | IC$_{50}$ value (µM) against EAC cells | | IC$_{50}$ value (µM) against PBMC cells | |
|---|---|---|---|---|---|---|---|---|---|---|
| | Trypan blue assay IC$_{50}$ value (µM) | MTT assay IC$_{50}$ value (µM) | Trypan blue assay IC$_{50}$ value (µM) | MTT assay IC$_{50}$ value (µM) | Trypan blue assay IC$_{50}$ value (µM) | MTT assay IC$_{50}$ value (µM) | Trypan blue assay IC$_{50}$ value (µM) | MTT assay IC$_{50}$ value (µM) | Trypan blue assay IC$_{50}$ value (µM) | MTT assay IC$_{50}$ value (µM) |
| BAMC | 4.6 ± 1.1 | 4.5 ± 2.0 | 5.2 ± 1.3 | 4.9 ± 0.2 | 5.8 ± 0.7 | 5.6 ± 1.0 | 6.8 ± 1.4 | 6.7 ± 1.8 | 85.7 ± 0.7 | 89.9 ± 3.5 |
| Cisplatin | 6.7 ± 0.5 | 5.9 ± 0.5 | 6.6 ± 0.2 | 5.9 ± 1.0 | 6.4 ± 1.8 | 6.5 ± 0.5 | 4.4 ± 1.3 | 4.9 ± 1.1 | 96.1 ± 0.8 | 91.4 ± 1.1 |

Compound BAMC was found to exhibit a promising anti-angiogenesis effect in MTT and trypan blue assays with IC$_{50}$ values of ~5.5 µM. Remarkably, compound BAMC exhibited very small toxicity ~97 µM to NIH-3T3 cells. Altogether, these results suggest that compound BAMC was potent and prone to exhibit a cytotoxic effect against cells of different origin. The unique structure of compound BAMC facilitates anti-angiogenesis activity of the compound. Hence, compound BAMC was investigated for its in vitro, in vivo and in silico activities.

Example 21

Anti-Mitogenicity and Tumor Cell Apoptosis

Figure 2A:
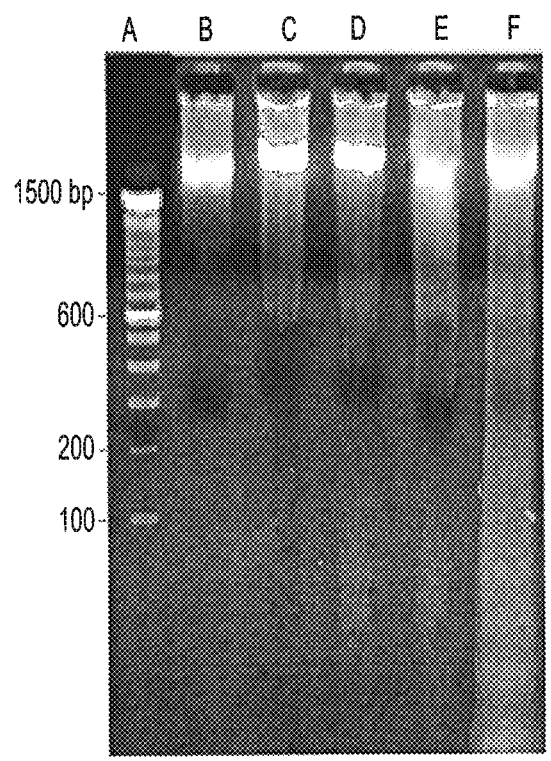
FIG. 2A depicts agarose gel electrophoresis for DNA fragmentation assay (apoptotic ladder) showing lane A as a marker (DNA ladder), lane B as a control, lane C having cells treated with 5 µM of compound BAMC, lane D having cells treated with 25 µM of compound BAMC, lane E having cells treated with 50 µM of compound BAMC, and lane F being the standard.
Figure 2B:
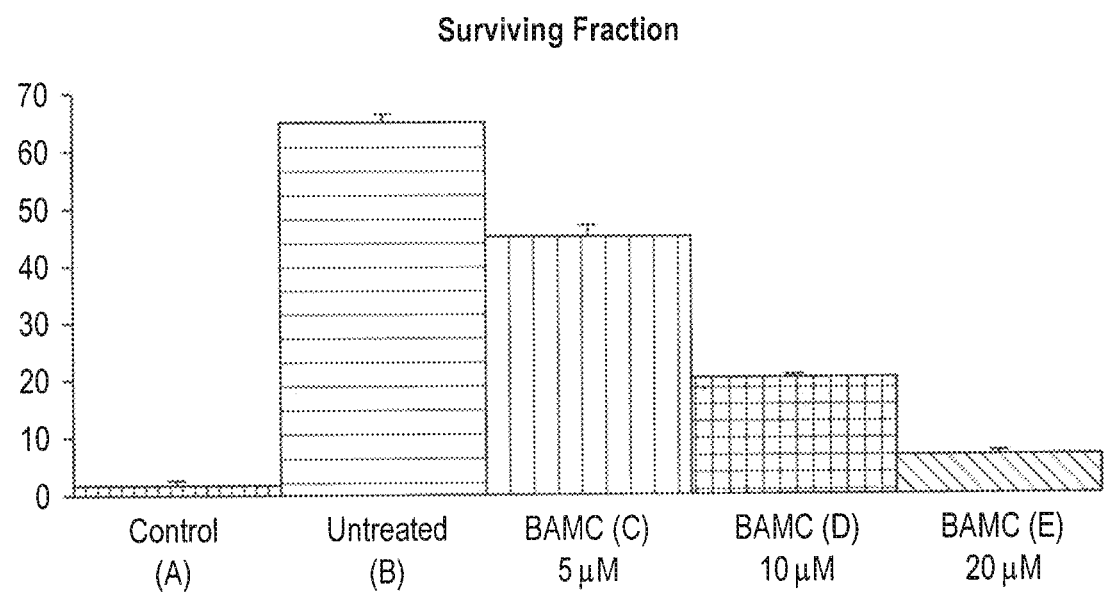
FIG. 2B is a graph showing extent of restraining of colony formation.

The colony formation assay was used to investigate the long term anti-mitogenicity of the cytotoxic molecules on cancer cell proliferation. Reticence in colony formation is considered a prolonged cytotoxic effect of the active biomolecule. In this analysis, A549 cells were treated with or without compound BAMC for analyzing long term effects. Results revealed that the compound BAMC visibly diminished the colonogenic efficiency of MCF-7 cells. As shown in FIGS. 2A and 2B, the compound BAMC was found to inhibit colony formation of MCF cells. In FIG. 2A, Lane A shows results obtained with the negative control (10 µM), Lane B shows results obtained with the control (100 µM), Lanes C-E show results obtained with compound BAMC at 5 µM, 10 µM, and 20 µM concentrations, respectively, compared to the standard cisplatin (Lane F). MCF-7 cells were pretreated (A) 10 µM (negative control), (B) 100 µM (control), (C) 5 µM of compound BAMC, (D) 10 µM of compound BAMC, and (E) 20 µM of compound BAMC for 6 hours and incubated for a period of 12 days to form colonies. Density of the colony formation was remarkably reduced by compound BAMC (FIG. 2B). Additionally, degradation of DNA into multiple inter-molecular small fragments of 180-200 base pairs is a distinct biochemical trait of apoptosis. Nuclear DNA treated with or without compound BAMC was analyzed by agarose gel electrophoresis. The results confirmed the typical "ladder (A)" formation of DNA treated with compound BAMC, whereas the DNA from untreated (B) cells did not show any changes. This study confirms that anti-angiogenesis effects of compound BAMC are mediated through apoptosis, leading to DNA degradation FIG. 2A.

Figure 3A:
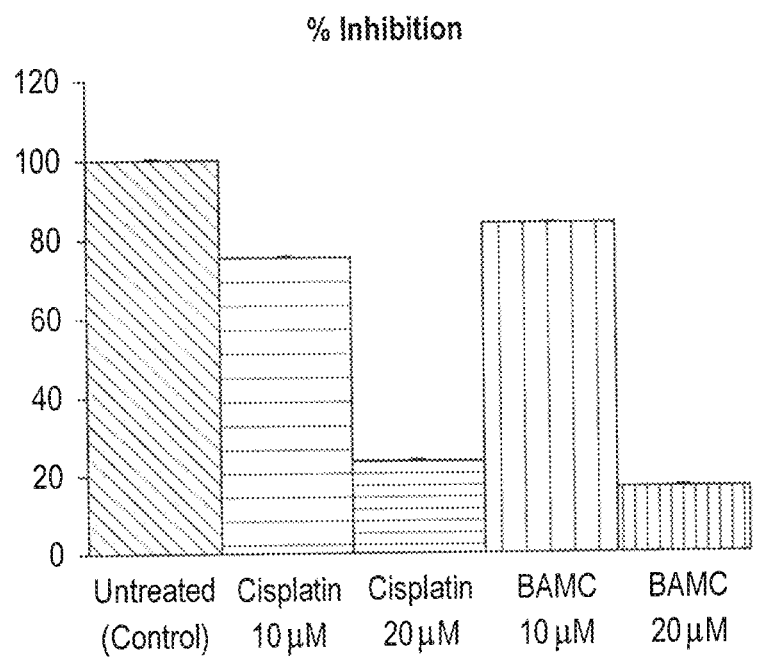
FIG. 3A is a graph showing extent of inhibition of A549 cancer cell migration.
Figure 3B:
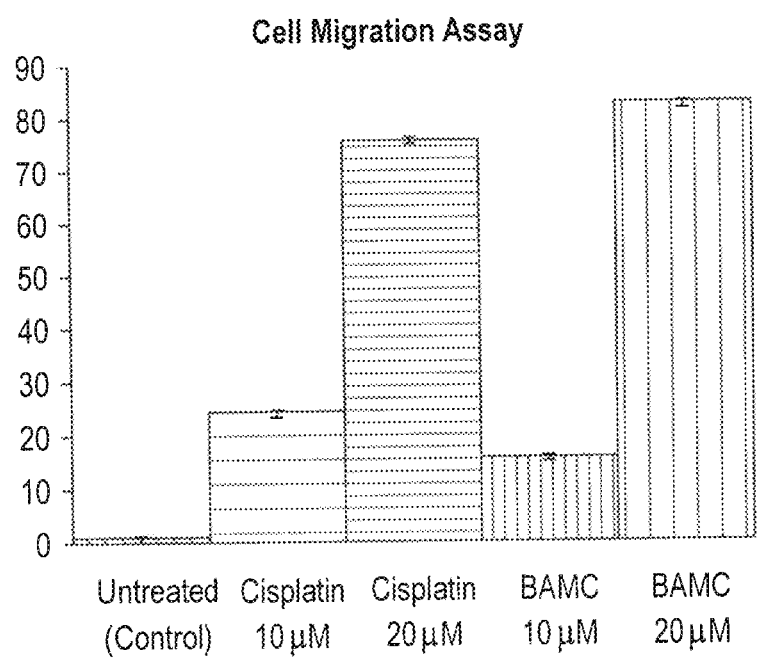
FIG. 3B is a graph showing cancer cell migration (statistically significant values are expressed as *p<0.05 and **p<0.01).

Most cancers, including MCF-7, Hela, A549, and EAC, are extremely metastatic with increased migration and invasive characteristics. To understand the role of compound BAMC in migration, a scratch wound assay was performed with A549 cells, which is highly in vitro migratory. Cell migration into the wound was quantified by taking snapshot pictures with a regular inverted microscope at 0, 24 and 48 h post scratch. The A549 cells migrated over a period of 48 h to fill the wound, however, compound BAMC treated cells failed to migrate into the wound and depicted a 72.33% and 12.99% inhibition of migration at 20 µM and 10 µM respectively (FIGS. 3A-3B). Therefore, compound BAMC has the potency to counteract angiogenesis and metastasis by targeting cancer cell migration.

Example 22

Caspase-3 Activation Analysis

Figure 4:
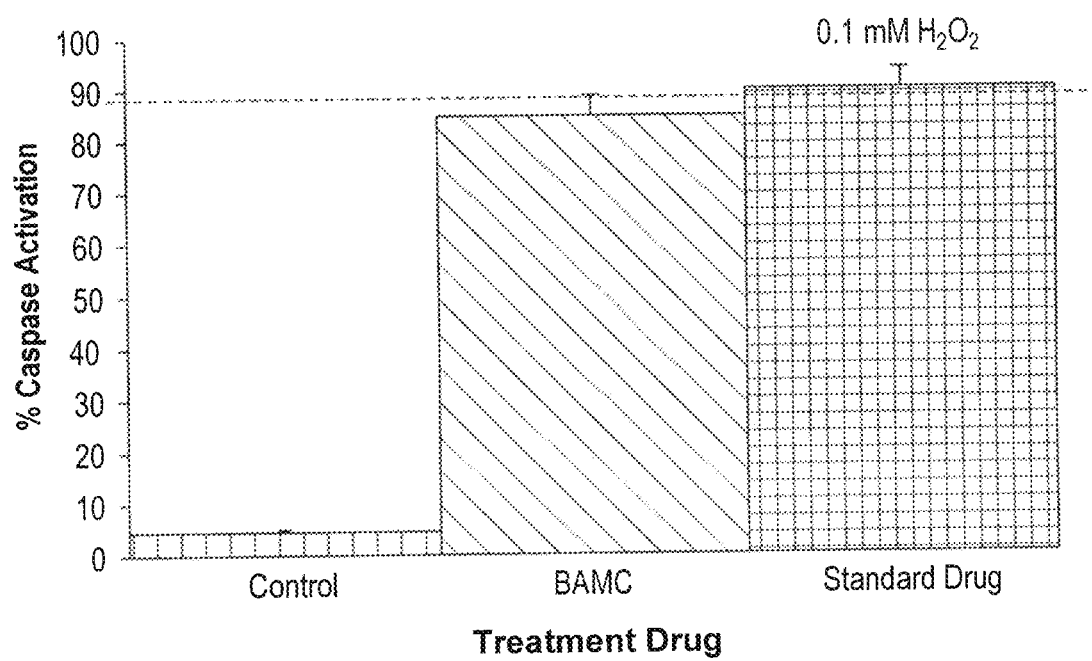
FIG. 4 is a graph showing percentage of caspase-3 activation by BAMC compound compared with V (10 µM of a standard drug) and 0.1 mM $H_2O_2$ as positive controls.

Caspase-3 serves as a convergence point for different apoptotic signalling pathway. Hence, the study explored the activation of this protein in breast cancer cells where it is said to be inactive. In this study, the compound BAMC demonstrated significant (P<0.05) caspase-3 activation in MCF-7 as shown in FIG. 4. BAMC demonstrated a high percentage of caspase-3 activation of 84.5, which was comparable to that of 90.3% by 10 µM standard drug and 91.1% by 0.1 mM $H_2O_2$.

Example 23

In Vivo Effect of Compound BAMC on Tumor Growth

Morpholine derivatives are known to be pharmacologically effective molecules against various pathological conditions including, cancer and inflammation, where inflammation of lymphoid organs is the common side effect in chemotherapy. Ehrlich ascites carcinoma (EAC) is the standard experimental animal model for assessing in vivo tumor growth and for the study of angiogenesis. Ascites tumor models of mouse origin is a reliable model system for initial pilot screening and it plays a crucial role in the drug designing process. Ascites secrete cell implantation provides a typical microenvironment by inducing local inflammation, amplified vascular permeability and intense edema formation and cellular migration. The mouse mammary carcinoma cells are known to secrete the ascites fluid which is a nutritional source for the growth factor of tumor cells, while a decrease in ascites fluids accounts for inhibition of tumor growth. Further, the results can be supported by measurement of neovascularisation or micro vessel density (MVD), which is a widely used surrogate indicator in pathological specimens and tumor models to assess the scenario of the disease. Extensive neovascularization has a direct association with tumor progression and its inhibition results in waning of tumor growth.

Figure 5A:
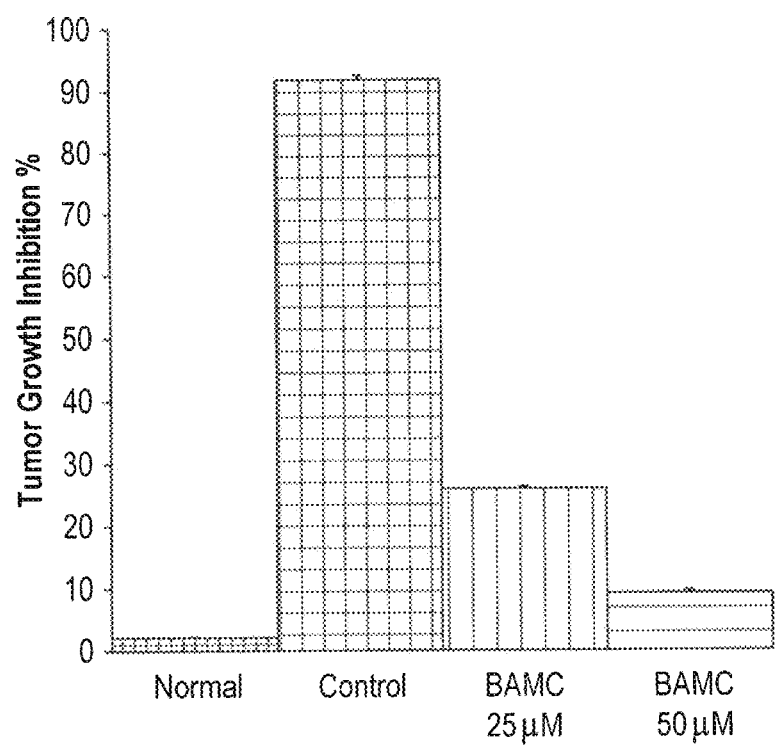
FIG. 5A is a graph showing decrease in body weight of mice treated with compound BAMC compared with control mice.
Figure 5B:
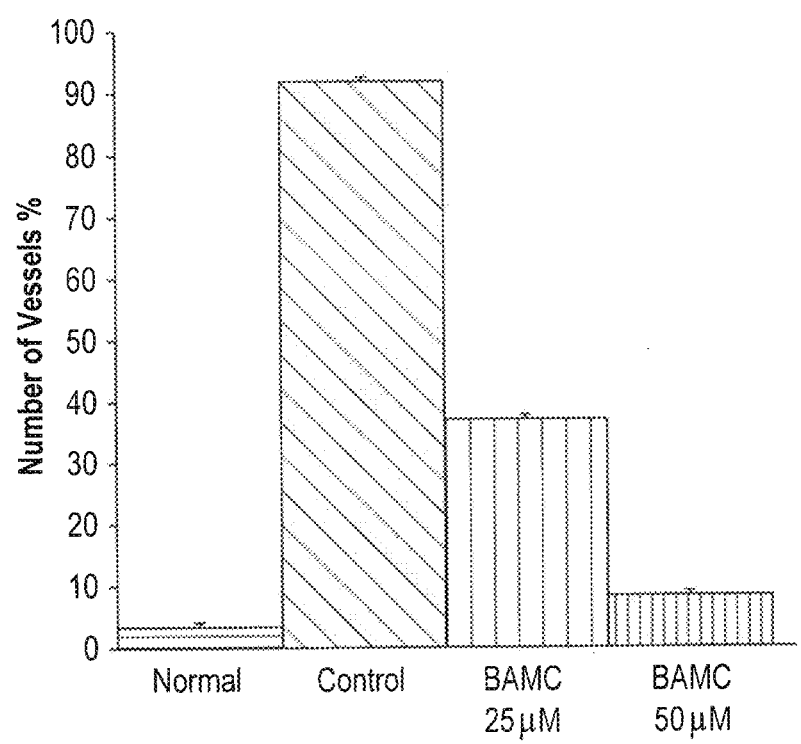
FIG. 5B is a graph showing MVD counts of the peritoneal of control- and compound 8f-treated tumor-bearing mice.

In the current investigation, the effect of compound BAMC on tumor growth, EAT cell number, ascites volume and peritoneal angiogenesis showed the potency of the compound against tumor development. Gradual increase in body weight of EAT bearing mice was observed. An exponential phase of growth was attained from the 6th day to the 12$^{th}$ day. In contrast, a significant decrease in body weight was observed in EAT bearing mice treated with compound BAMC. EAC tumor models were administered with three doses of compound BAMC at 25 mg/kg and 50 mg/kg body weight (bw) on every alternative day. The experimental results indicate that compound BAMC decreased the tumor volume by 74.35% and 80.2% of inhibition in a dose dependent manner, which resulted in diminished cell density with six fold reduction in a concentration dependent manner (FIGS. 5A-5B). The administration of compound BAMC did not show any symptoms of adverse effect on the normal lymphoid organs which was evident from the morphology of the kidney, liver and spleen of treated and untreated groups. Moreover, inhibition of tumor growth by compound BAMC prompted an investigation on anti-angiogenic efficacy on neovascularization by reliable models such as rVEGF$_{165}$ tumor induced peritoneal angiogenesis assay. The results demonstrate that the compound BAMC regressed EAC induced angiogenesis in peritoneum with 40% and 15% respectively in a concentration dependent manner. Hence, BAMC compound exhibited anti-proliferative effects against multiple cancer cell lines and mediated angio-prevention tumor growth.

VEGF, key binding residues in the active site of the model were determined and proved. This important evidence proves the relative significance of each residue in a positive restricting interaction, showing the binding energy, ligand efficiency, inhibition constant, van der Waals forces, hydrogen bond, dissolve energy, bonding residues score, and bond length score for the active site of VEGF-BAMC complex, compared to the compound BAMC, provided in Table 2 below.

TABLE 2

Dock Score Results of compound BAMC with VEGF PDB cod VEGFr (3qtk)

| Conformation | Binding energy (kJ mol$^{-1}$) | Ligand efficiency | Inhibition constant | vDW + H-bond + desolv energy | No. of H-bonds | Bonding residues | Bond length (Å) |
|---|---|---|---|---|---|---|---|
| S1 | −6.92 | −0.25 | 8.53 | −7.58 | 1 | 3qtk:A:CYS61:O | 1.923 |
| S2 | −7.48 | −0.27 | 3.31 | −8.47 | 1 | 3qtk:A:GLN30:OE1 | 2.131 |
| S3 | −7.42 | −0.27 | 3.65 | −8.30 | 1 | 3qtk:A:GLY52:HN | 1.889 |
| S4 | −7.27 | −0.26 | 4.73 | −7.94 | 1 | 3qtk:A:GLY52:HN | 1.937 |
| S5 | −6.44 | 3-0.22 | μM | −7.39 | 1 | 3qtk:A:GLN30:OE | 1.977 |
| S6 | −7.74 | −0.28 | μM | −8.33 | 2 | 3qtk:D:ASP56:HN 3qtk:D:CYS61:HN | 2.006 |
| S7 | −6.57 | −0.23 | μM | −7.64 | 1 | 3qtk:D:GLY52:HN | 1.940 |
| S8 | −6.40 | −0.23 | μM | −6.63 | 1 | 3qtk:A:LYS41:HZ1 | 2.244 |
| S9 | −7.44 | −0.27 | μM | −9.53 | — | — | — |
| S10 | −5.84 | −0.21 | μM | −6.66 | 3 | 3qtk:C:GLN72:OE1 3qtk:C:GLN72:HE21 3qtk::B:MET11:HN | 2.002 2.191 2.954 |

Example 24

Molecular Docking Studies in Silico Validation

Figure 6:
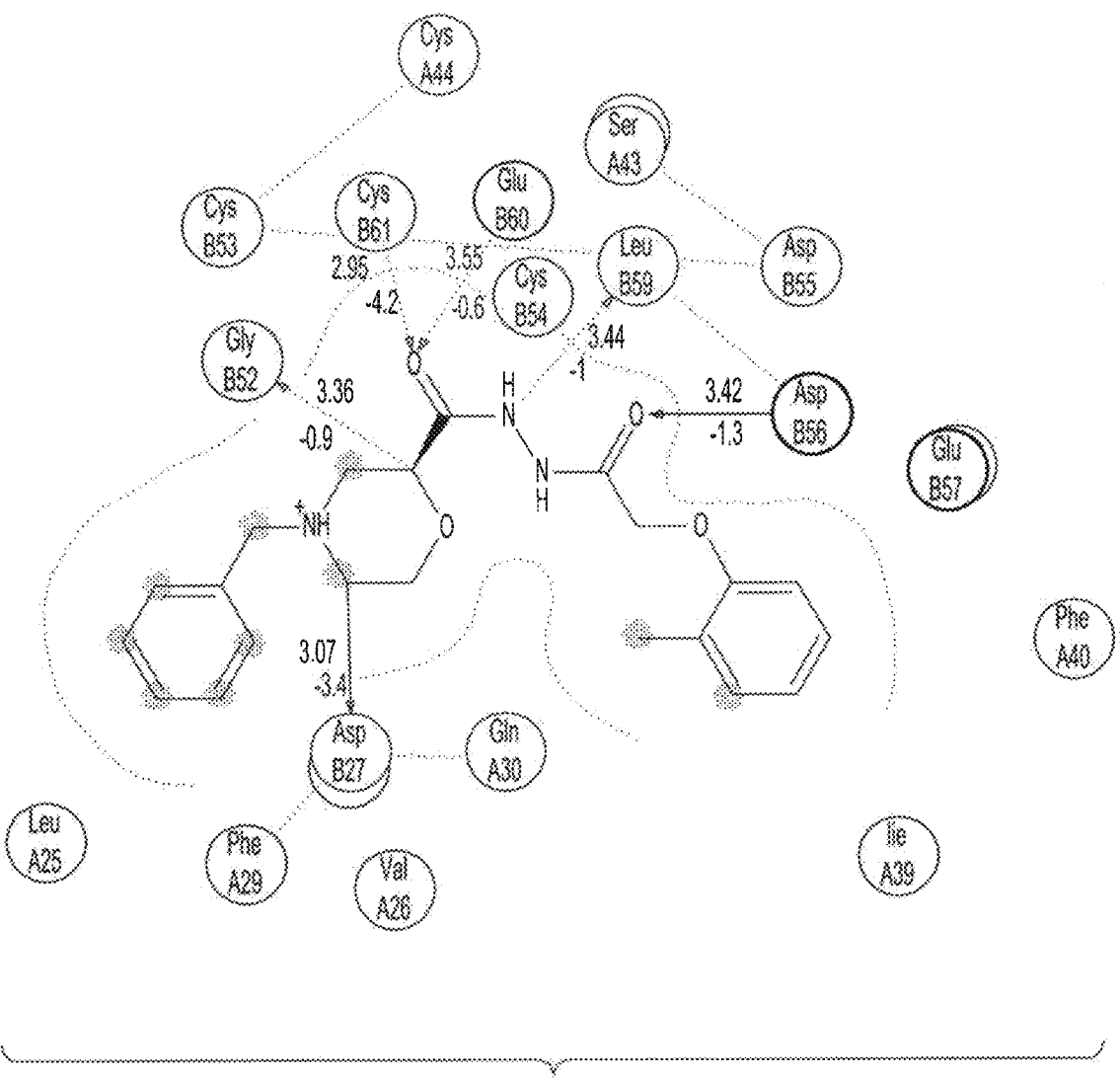
FIG. 6 shows 2D interactions analysis of compound BAMC with VEGFr.
Figure 7:
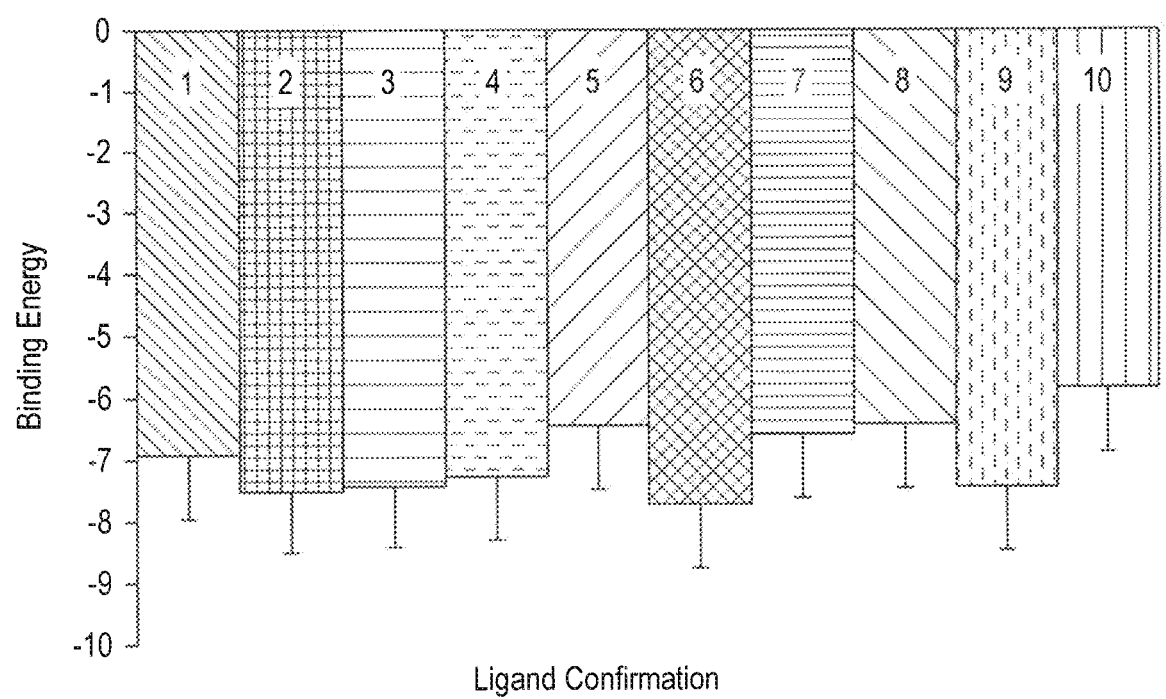
FIG. 7 is a graph showing binding energy of compound BAMC with rVEGF at the conformation S6 with the lowest binding energy of −7.74 kJ/mol (statistically significant values are expressed as *p<0.05 and **p<0.01)
Figure 8:
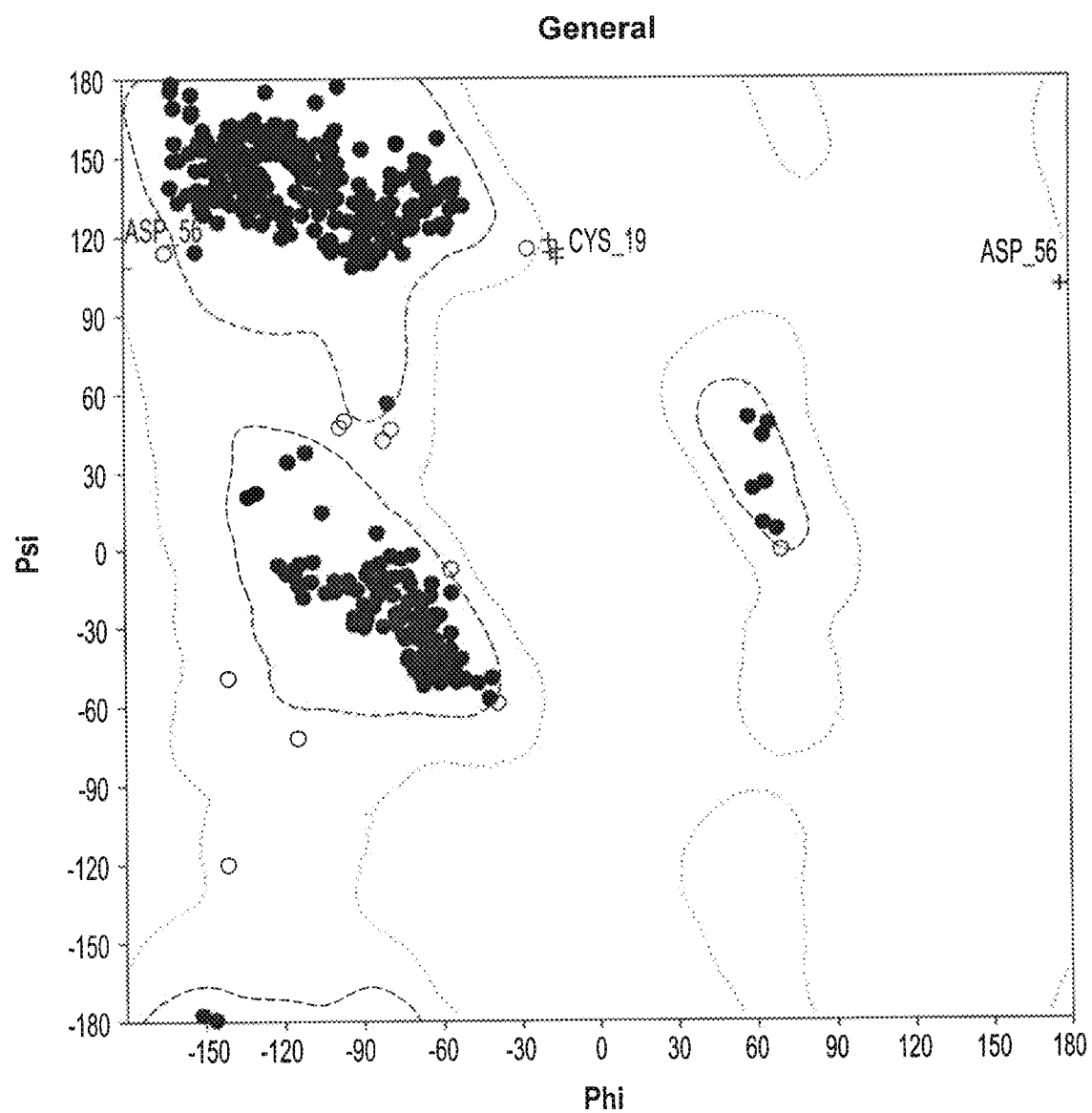
FIG. 8 depicts a Phi Psi plot showing protein geometry of 3qtk amino acids in protein structure.

The autodock programme was utilized to produce the protein-BAMC complex in order to understand the interaction between VEGF protein and ligand BAMC. It was clearly seen that ligand BAMC was placed in the center of the active site and stabilized by hydrogen bonding interactions. The hydrogen bonds exhibited in the VEGF-BAMC complex were documented, together with their distances and angles, by taking into account the interaction energies of the compound BAMC with residues in the active site of the The VEGF-9d complex has binding energy −7.74 kJ/mol (FIG. 7). It was proved by the interaction analysis that CYS61 and ASP56, the amino acid residues of the VEGF, were attached significantly to the compound BAMC as the main providers for the inhibition interaction (FIG. 6). Through the in silico study, it was proved that amino acid CYS61 and ASP56 are the most preferred residues in the inhibitor binding reaction and that the interaction energy does not include a contribution from the water or the expanded protein structure. A list of hydrogen bond interactions between the protein and active site was generated. The VEGF structure was further applied for protein-ligand modeling studies. Positively connected with receptor binding, docking in VEGF protein plays a crucial role in sustaining a functional conformation. In this study, the interactions between the VEGF and the inhibitors are of great use in revealing and understanding the possible mechanism of inhibitor binding. In the VEGF structure, just as in other biological molecules, it is apparent that hydrogen bonds play a significant role. CYS61 and ASP56 are important for strong hydrogen bonding interactions with inhibitors. It is obvious that BAMC is the most likely inhibitor and the CYS61 and ASP56 residues are involved in inhibitor binding and they form hydrogen bonds with the inhibitors. It should be taken into consideration that the CYS61 and ASP56 are vital for receptor binding or preserving the hydrophobicity of the inhibitor binding pocket. Similarly, repetitive values in the region of phi=−150 to −140 and psi=+120 to +135 give extended chains with conformations that allow interactions between closely folded parallel segments (beta sheet structures). The structure of VEGF-BAMC complex is composed mostly of beta sheets and the Phi Psi plot shows a broad range of values in the −150, +120 region as shown in FIG. 8.

It is to be understood that the present subject matter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound of the structural formula:

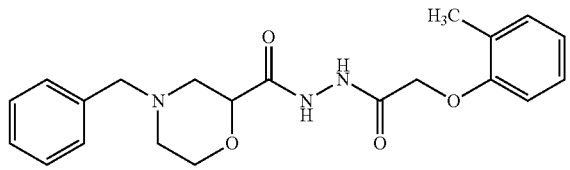 [SMILES: Cc1ccccc1OCC(=O)NNC(=O)C1CN(Cc2ccccc2)CCO1]

or a pharmaceutically acceptable salt thereof.

2. A pharmaceutical composition comprising the compound of claim 1 and a pharmaceutically acceptable carrier.

3. The pharmaceutical composition of claim 2, wherein the pharmaceutically acceptable carrier is selected from the group consisting of binders, suspending agents, lubricants, flavorings, sweeteners, preservatives, dyes, and coatings.

4. The pharmaceutical composition of claim 2, further comprising an additive selected from the group consisting of water, glycols, oils, alcohols, flavoring agents, preservatives, and coloring agents.

5. The pharmaceutical composition of claim 2, further comprising an additive selected from the group consisting of starches, sugars, diluents, granulating agents, lubricants, binders, and disintegrating agents.

6. The pharmaceutical composition of claim 2, wherein the pharmaceutical composition is compounded in a unit dosage form, the unit dosage form selected from the group consisting of tablets, pills, capsules, powders, granules, ointments, sterile parenteral solutions, sterile suspensions, metered aerosol sprays, metered liquid sprays, drops, ampules, auto-injector devices, and suppositories.

7. A method of treating cancer, comprising the step of administering to a patient in need thereof a therapeutically effective amount of the pharmaceutical composition according to claim 2.

8. The method of claim 7, wherein the cancer is selected from the group consisting of breast cancer and lung cancer.

9. A method of treating cancer, comprising administering to a patient in need thereof a pharmaceutical composition comprising a compound having the following structural formula:

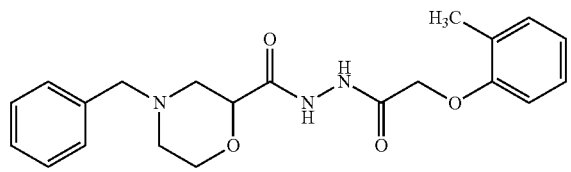 [SMILES: Cc1ccccc1OCC(=O)NNC(=O)C1CN(Cc2ccccc2)CCO1]

or a pharmaceutically acceptable salt thereof.

10. The method of claim 1, wherein the cancer is selected from the group consisting of breast cancer and lung cancer.

* * * * *